(12) United States Patent
Gan et al.

(10) Patent No.: US 6,936,379 B2
(45) Date of Patent: Aug. 30, 2005

(54) METHOD FOR ELECTRODE DESIGN FOR IMPLANTABLE DEVICE APPLICATIONS THAT REQUIRE THE ELECTIVE REPLACEMENT INDICATOR (ERI)

(75) Inventors: Hong Gan, East Amherst, NY (US); Esther S. Takeuchi, East Amherst, NY (US)

(73) Assignee: Wilson Greatbatch Technologies, Inc., Clarence, NY (US)

( * ) Notice: Subject to any disclaimer, the term of this patent is extended or adjusted under 35 U.S.C. 154(b) by 471 days.

(21) Appl. No.: 10/290,858

(22) Filed: Nov. 8, 2002

(65) Prior Publication Data

US 2003/0104269 A1 Jun. 5, 2003

Related U.S. Application Data

(60) Provisional application No. 60/345,031, filed on Nov. 9, 2001.

(51) Int. Cl.[7] ................................................. H01M 4/58
(52) U.S. Cl. ..................................................... 429/231.5
(58) Field of Search ................................. 429/168, 217, 429/220, 221, 224, 231.5, 231.8, 231.95, 232, 245

(56) References Cited

U.S. PATENT DOCUMENTS 5,370,668 A    12/1994  Shelton et al.
5,569,553 A  * 10/1996  Smesko et al. ............... 429/90

FOREIGN PATENT DOCUMENTS

EP    1 150 366 A2    4/2001
EP    1 150 366 A3    10/2002

* cited by examiner

Primary Examiner—Dah-Wei D. Yuan
Assistant Examiner—Ben Lewis
(74) Attorney, Agent, or Firm—Michael F. Scalise

(57) ABSTRACT

A method for providing a physician with an elective replacement indicator (ERI) for an implantable medical device is described. The medical device is powered by an electrochemical having a lithium anode coupled to a sandwich cathode comprising the configuration: SVO/current collector/$CF_x$, with the SVO facing the anode. The indicator is predicated on when the cell's discharge capacity is nearing end-of-life (EOL) based on the theoretical capacity and the discharge efficiency of the SVO and $CF_x$ active materials. This serves as an indicator when it is time to replace the medical device.

34 Claims, 2 Drawing Sheets

METHOD FOR ELECTRODE DESIGN FOR IMPLANTABLE DEVICE APPLICATIONS THAT REQUIRE THE ELECTIVE REPLACEMENT INDICATOR (ERI)

CROSS-REFERENCE TO RELATED APPLICATION

This application claims priority from provisional application Ser. No. 60/345,031, filed Nov. 9, 2001.

BACKGROUND OF THE INVENTION

1. Field of Invention

This invention relates to the conversion of chemical energy to electrical energy. In particular, the present invention relates to an implantable medical device powered by an alkali metal electrochemical cell, such as of lithium coupled with a sandwich cathode. The sandwich cathode design comprises a second cathode active material of a relatively high energy density but of a relatively low rate capability sandwiched between two current collectors with a first cathode active material having a relatively low energy density but of a relatively high rate capability in contact with the opposite sides of the current collectors. The present invention then provides an indicator as to when the cell's discharge capacity is nearing end-of-life (EOL) based on the theoretical capacity and the discharge efficiency of the first and second cathode active materials. This early warning is defined as the elective replacement indicator (ERI) and signals a physician when it is time to replace the medical device. Suitable medical devices include cardiac defibrillators, neurostimulators, pacemakers, and the like.

2. Prior Art

In implantable medical device applications, it is important to be able to accurately predict when the batteries powering the device will reach their end of life. For patient safety, doctors need to have this information several months before the battery reached the end of its service life. This gives them time to schedule the patient for replacement of the implantable device.

Historically, the Li/SVO cell system has been used as the power source for implantable cardiac defibrillator applications requiring high rate pulse capability, i.e., about 1 to 4 about 4 amps. Since Li/SVO cells have a staged discharge voltage profile, a pre-determined background voltage is generally used as the ERI. This pre-determined voltage value varies depending on the cell size, theoretical capacity and the associated device design. Additionally, due to the characteristic voltage delay and Rdc growth that occurs at about the 2.6-volt plateau, a pre-determined Rdc or voltage value under high current pulsing is sometimes used as an ERI indicator. Consequently, the ERI indicator selection is very complicated and dependent on the individual device design of each manufacturer.

The Li/$CF_x$ system provides medium rate discharge capability (mA range). This cell is a good power source for devices like implantable neurostimulators and implantable devices that treat cardiac heart failure (CHF). Although the Li/$CF_x$ system has very high energy density, its discharge voltage profile is mostly flat (~2.8V). Near the end of discharge, however, a sharp voltage drop occurs. This unfavorable characteristic voltage profile makes it very difficult to set the ERI accurately for Li/$CF_x$ cells. In order to resolve this problem, mixtures of $CF_x$ and other cathode materials, for example SVO, are proposed.

U.S. patent application Ser. No. 09/560,060, filed Apr. 27, 2000, titled "Sandwich Cathode Design For Alkali Metal Electrochemical Cell With High Discharge Rate Capability" is assigned to the assignee of the present invention and incorporated herein by reference. This application describes a cathode construction with the configuration of: first cathode active material/current collector/second cathode active material/current collector/first cathode active material. In this design, the first cathode active material has a relatively lower energy density but a relatively higher power capability than that of the second cathode active material. In a design of: first cathode active material/current collector/second cathode active material, the first material always faces the anode. While the concept of using these types of electrodes in electrochemical cells has been disclosed, the utilization of such a system to address the ERI/EOL issue remains unresolved. In the present invention, the utilization of this cathode design concept to address the ERI/EOL issue is discussed.

SUMMARY OF THE INVENTION

The previously discussed U.S. patent application Ser. No. 09/560,060 describes contacting two types of electrode active materials to the opposite sides of a cathode current collector. One of the electrode materials provides a relatively higher discharge rate capability (SVO for example), while the other has a relatively higher energy density ($CF_x$ for example). In other words, the first electrode active material has higher conductivity (or lower resistance) than that of the second material, while it has lower energy density (volumetrically or gravimetrically) than that of the second material. Therefore, in order for the cell to function properly, the first electrode active material always faces the counter electrode—the anode. One example of such a cathode configuration is: SVO/current collector/$CF_x$/current collector/SVO. Another example is: SVO/current collector/$CF_x$ with the SVO side facing the lithium anode.

In these designs, several voltage plateaus characterize the cell's discharge profile. Initially, the profile primarily follows the 3.2 voltage plateau of the SVO material. When the cell voltage drops to about 2.8 volts, another plateau primarily contributed by the $CF_x$ material is reached. When the profile reaches the 2.6 voltage plateau, the contribution is again primarily that of the SVO material. From about 2.5 volts to end EOL (~2.0V) both the SVO and $CF_x$ materials contribute to the discharge.

Based on this, the capacity contribution from each voltage plateau region during cell discharge is dependent on the initial capacity ratio between the SVO and $CF_x$ materials in the cathode construction. By controlling the ratio of SVO to $CF_x$ in the cathode, it is possible to control the capacity contribution of the cell at various voltage plateau regions. For any device application, if the ERI voltage is defined as about 2.6 volts (or any voltage between about 2.65 volts to about 2.5 volts) and EOL is defined as about 2.4 volts (or any voltage between about 2.5 volts to about 2.0 volts, or even lower for low rate cells), varying the SVO to $CF_x$ capacity ratio provides a means for calculating both ERI and EOL. In other words, a mechanism for determining both EOL and ERI is provided by varying the relative weight of SVO to $CF_x$ in a cathode having one of the following configurations: SVO/current collector/$CF_x$/current collector/SVO, SVO/current collector/SVO/$CF_x$/SVO/current collector/SVO, SVO/current collector/$CF_x$ with the SVO facing the anode, and SVO/current collector/SVO/$CF_x$ with the SVO facing the anode. By adjusting the SVO to $CF_x$ weight ratio, the capacity ratio of SVO:$CF_x$ is achieved ranging from 1:50 to 10:1. In addition, since the cathode is not a mixture, but discrete layers of the active materials, the rate capability is not compromised by changes in the SVO/$CF_x$ ratio.

These and other objects of the present invention will become increasingly more apparent to those skilled in the art by reference to the following description and to the appended drawings.

DETAILED DESCRIPTION OF THE PREFERRED EMBODIMENTS

Figure 1:
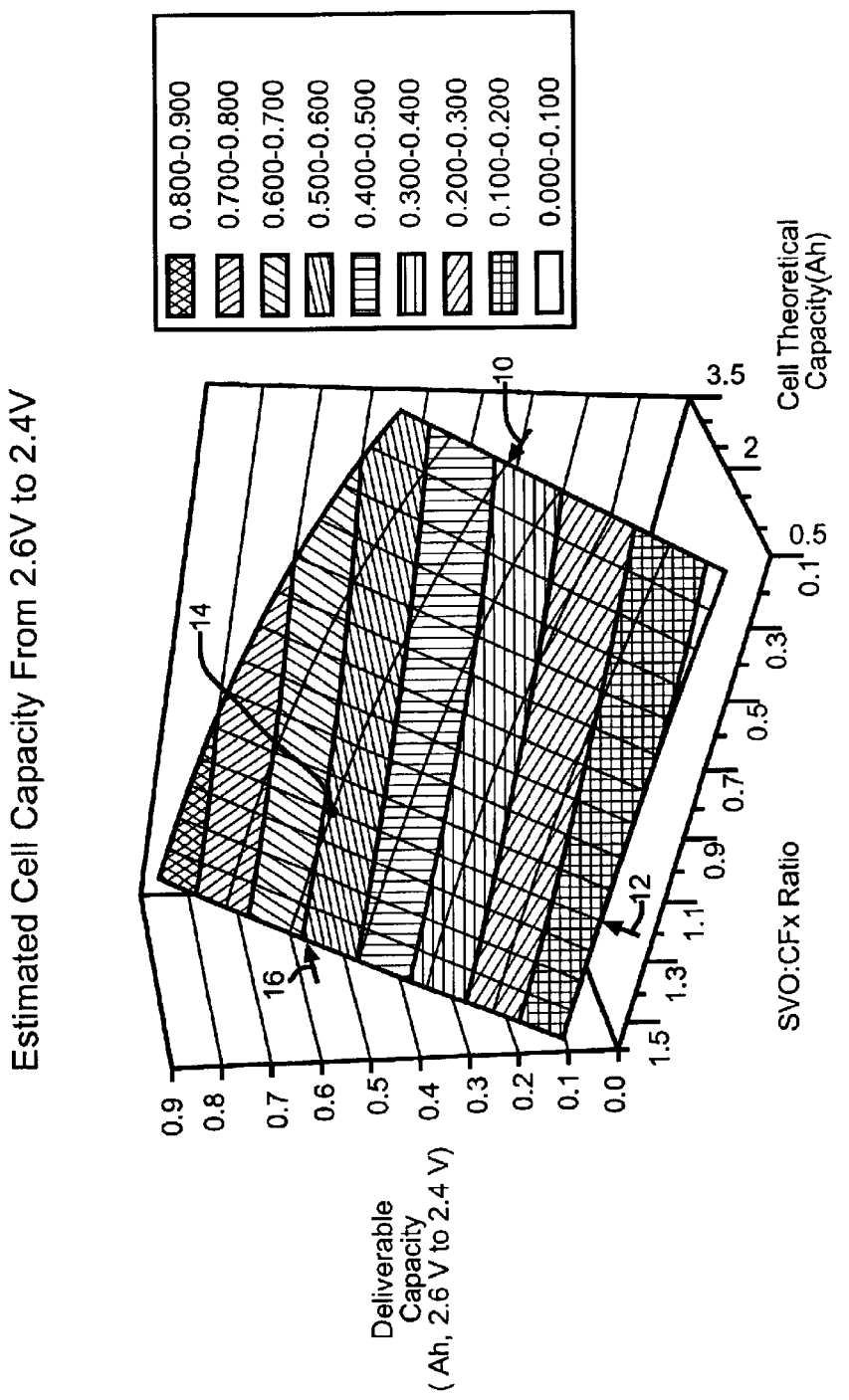
FIG. 1 is a graph of the estimated capacity from about 2.6 volts to about 2.4 volts of a cell having a lithium anode couples to an $SVO/CF_x$ sandwich cathode.

As used herein, the term "pulse" means a short burst of electrical current of significantly greater amplitude than that of a pre-pulse current immediately prior to the pulse. A pulse train consists of at least two pulses of electrical current delivered in relatively short succession with or without open circuit rest between the pulses. An exemplary pulse train may consist of four 10-second pulses of about 0.5 mA/cm$^2$ to about 50 mA/cm$^2$ with a 15 second rest between each pulse.

An electrochemical cell that possesses sufficient energy density and discharge capacity required to meet the vigorous requirements of implantable medical devices comprises an anode of a metal selected from Groups IA, IIA and IIIB of the Periodic Table of the Elements. Such anode active materials include lithium, sodium, potassium, etc., and their alloys and intermetallic compounds including, for example, Li—Si, Li—Al, Li—B and Li—Si—B alloys and intermetallic compounds. The preferred anode comprises lithium. An alternate anode comprises a lithium alloy such as a lithium-aluminum alloy. The greater the amounts of aluminum present by weight in the alloy, however, the lower the energy density of the cell.

The form of the anode may vary. Preferably the anode is a thin metal sheet or foil of the anode metal pressed or rolled on a metallic anode current collector, preferably comprising titanium, titanium alloy or nickel. Copper, tungsten and tantalum are also suitable materials for the anode current collector. The anode current collector has an integral tab or lead contacted by a weld to a cell case of conductive metal in a case-negative electrical configuration. Alternatively, the anode may be formed in some other geometry, such as a bobbin shape, cylinder or pellet to allow an alternate low surface cell design.

The electrochemical cell further comprises a cathode of electrically conductive cathode active materials. The cathode is preferably of solid active materials and the electrochemical reaction at the cathode involves conversion of ions that migrate from the anode to the cathode into atomic or molecular forms. The cathode may comprise a first active material of a metal element, a metal oxide, a mixed metal oxide and a metal sulfide, and combinations thereof and a second active material of a carbonaceous chemistry. The first cathode active material has a relatively lower energy density but a relatively higher rate capability than the second cathode active material.

The first cathode active material is formed by the chemical addition, reaction, or otherwise intimate contact of various metal oxides, metal sulfides and/or metal elements, preferably during thermal treatment, sol-gel formation, physical vapor deposition, chemical vapor deposition or hydrothermal synthesis in mixed states. The active materials thereby produced contain metals, oxides and sulfides of Groups IB, IIB, IIIB, IVB, VB, VIB, VIIB and VIII, which includes the noble metals and/or other oxide and sulfide compounds.

One preferred metal oxide of a relatively high rate capability but a relatively low energy density has the general formula $SM_xV_2O_y$ where SM is a metal selected from Groups IB to VIIB and VIII of the Periodic Table of Elements, wherein x is about 0.30 to 2.0 and y is about 4.5 to 6.0 in the general formula. By way of illustration, and in no way intended to be limiting, one exemplary cathode active material comprises silver vanadium oxide having the general formula $Ag_xV_2O_y$ in any one of its many phases, i.e., β-phase silver vanadium oxide having in the general formula x=0.35 and y=5.8, γ-phase silver vanadium oxide having in the general formula x=0.74 and y=5.37 and ε-phase silver vanadium oxide having in the general formula x=1.0 and y=5.5, and combination and mixtures of phases thereof. For a more detailed description of such cathode active materials reference is made to U.S. Pat. No. 4,310,609 to Liang et al. This patent is assigned to the assignee of the present invention and incorporated herein by reference.

Another preferred metal oxide cathode material of a relatively high rate capability but a relatively low energy density includes $V_2O_z$ wherein z≦5 combined with $Ag_2O$ with silver in either the silver(II), silver(I) or silver(0) oxidation state and CuO with copper in either the copper(II), copper(I) or copper(0) oxidation state. This mixed metal oxide has the general formula $Cu_xAg_yV_2O_z$, (CSVO) and the range of material compositions is preferably about 0.01≦z≦6.5. Typical forms of CSVO are $Cu_{0.16}Ag_{0.67}V_2O_z$ with z being about 5.5 and $Cu_{0.5}Ag_{0.5}V_2O_z$ with z being about 5.75. The oxygen content is designated by z since the exact stoichiometric proportion of oxygen in CSVO can vary depending on whether the cathode material is prepared in an oxidizing atmosphere such as air or oxygen, or in an inert atmosphere such as argon, nitrogen and helium. For a more detailed description of this cathode active material reference is made to U.S. Pat. No. 5,472,810 to Takeuchi et al. and U.S. Pat. No. 5,516,340 to Takeuchi et al., both of which are assigned to the assignee of the present invention and incorporated herein by reference.

The sandwich cathode design of the present invention further includes a second active material of a relatively high energy density and a relatively low rate capability in comparison to the first cathode active material. The second active material is preferably a carbonaceous compound prepared from carbon and fluorine, which includes graphitic and nongraphitic forms of carbon, such as coke, charcoal or activated carbon. Fluorinated carbon is represented by the formula $(CF_x)_n$ wherein x varies between about 0.1 to 1.9 and preferably between about 0.5 and 1.2, and $(C_2F)_n$ wherein the n refers to the number of monomer units which can vary widely.

In a broader sense, it is contemplated by the scope of the present invention that the first active material of the sandwich cathode design is any material which has a relatively lower energy density but a relatively higher rate capability than the second active material. In addition to silver vanadium oxide and copper silver vanadium oxide, $V_2O_5$, $MnO_2$, $LiCoO_2$, $LiNiO_2$, $LiMn_2O_4$, $TiS_2$, $Cu_2S$, FeS, $FeS_2$, copper oxide, copper vanadium oxide, and mixtures thereof are useful as the first active material. And, in addition to fluorinated carbon, $Ag_2O$, $Ag_2O_2$, $CuF_2$, $Ag_2CrO_4$, $MnO_2$, and even SVO itself, are useful as the second active material. The theoretical volumetric capacity (Ah/ml) of $CF_x$ is 2.42, $Ag_2O_2$ is 3.24, $Ag_2O$ is 1.65 and $AgV_2O_{5.5}$ is 1.37. Thus, $CF_x$, $Ag_2O_2$, $Ag_2O$, all have higher theoretical volumetric capacities than that of SVO.

Before fabrication into a sandwich cathode for incorporation into an electrochemical cell, the first and second active materials are preferably mixed with a binder material such as a powdered fluoro-polymer. More preferably, powdered polytetrafluoroethylene or powdered polyvinylidene fluoride are present in the cathode mixture at, by weight, about 1% to about 5%.

Further, up to about 10%, by weight, of a conductive diluent is preferably added to the cathode mixture to improve conductivity. Suitable materials for this purpose include acetylene black, carbon black and/or graphite or a metallic powder such as powdered nickel, aluminum, titanium and stainless steel. The preferred cathode active mixture thus includes, by weight, a powdered fluoro-polymer binder present at about 3%, a conductive diluent present at about 3% and about 94% of the cathode active material.

Cathode components for incorporation into an electrochemical cell according to the present invention may be prepared by rolling, spreading or pressing the first and second cathode active materials onto a suitable current collector selected from the group consisting of stainless steel, titanium, tantalum, platinum and gold. The preferred current collector material is titanium, and most preferably the titanium cathode current collector has a thin layer of graphite/carbon paint, gold, iridium, palladium, platinum, rhodium, ruthenium, and mixtures thereof provided thereon. Cathodes prepared as described above may be in the form of one or more plates operatively associated with at least one or more plates of anode material, or in the form of a strip wound with a corresponding strip of anode material in a structure similar to a "jellyroll".

According to one embodiment of the present invention, SVO cathode material, which provides a relatively high power or rate capability but a relatively low energy density or volumetric capability and $CF_x$ cathode material, which has a relatively high energy density but a relatively low rate capability, are individually pressed on opposite sides of a current collector, so that both materials are in direct contact therewith. Therefore, one exemplary cathode electrode has the following configuration:

$$SVO/\text{current collector}/CF_x/\text{current collector}/SVO \quad (1)$$

An important aspect of the present invention is that the high rate cathode material (in this case the SVO material) maintains direct contact with the current collector.

Another embodiment has the high capacity/low rate material sandwiched between the high rate cathode materials, in which the low rate/high capacity material is in direct contact with the high rate material. This cathode design has the following configuration:

$$SVO/\text{current collector}/SVO/CF_x/SVO/\text{current collector}/SVO \quad (2)$$

An important aspect of the present invention is that the high capacity material having the low rate capability is preferably positioned between two layers of high rate cathode material (either high or low capacities). This is shown in configurations 1 and 2 above. In other words, the exemplary $CF_x$ material never directly faces the lithium anode. In addition, the low rate cathode material must be short circuited with the high rate material, either by direct contact as demonstrated above in configuration 2, or by parallel connection through the current collectors as in configuration 1.

Additional embodiments have the configurations:

$$SVO/\text{current collector}/CF_x \quad (3)$$

$$SVO/\text{current collector}/SVO/CF_x \quad (4)$$

As described above with respect to configurations 1 and 2, in configurations 3 and 4 the exemplary $CF_x$ material never directly faces the lithium anode.

In order to prevent internal short circuit conditions, the sandwich cathode is separated from the Group IA, IIA or IIIB anode by a suitable separator material. The separator is of an electrically insulative material, is chemically unreactive with the anode and cathode active materials and is both chemically unreactive with and insoluble in the electrolyte. In addition, the separator material has sufficient porosity to allow flow there through of the electrolyte during the electrochemical reaction of the cell. Illustrative separator materials include fabrics woven from fluoropolymeric fibers including polyvinylidine fluoride, polyethylenetetrafluoroethylene, and polyethylenechlorotrifluoroethylene used either alone or laminated with a fluoropolymeric microporous film, non-woven glass, polypropylene, polyethylene, glass fiber materials, ceramics, a polytetrafluoroethylene membrane commercially available under the designation ZITEX (Chemplast Inc.), a polypropylene membrane commercially available under the designation CELGARD (Celanese Plastic Company, Inc.) and a membrane commercially available under the designation DEXIGLAS (C. H. Dexter, Div., Dexter Corp.).

The electrochemical cell of the present invention further includes a nonaqueous, ionically conductive electrolyte that serves as a medium for migration of ions between the anode and the cathode electrodes during the cell's electrochemical reactions. Nonaqueous electrolytes suitable for the present invention are substantially inert to the anode and cathode materials, and they exhibit those physical properties necessary for ionic transport, namely, low viscosity, low surface tension and wettability.

A suitable electrolyte has an inorganic, ionically conductive alkali metal salt dissolved in a mixture of aprotic organic solvents comprising a low viscosity solvent and a high permittivity solvent. Preferably, the salt is selected from $LiPF_6$, $LiBF_4$, $LiAsF_6$, $LiSbF_6$, $LiClO_4$, $LiO_2$, $LiAlCl_4$, $LiGaCl_4$, $LiC(SO_2CF_3)_3$, $LiN(SO_2CF_3)_2$, $LiSCN$, $LiO_3SCF_3$, $LiC_6F_5SO_3$, $LiO_2CCF_3$, $LiSO_6F$, $LiB(C_6H_5)_4$ and $LiCF_3SO_3$, and mixtures thereof.

Low viscosity solvents useful with the present invention include esters, linear and cyclic ethers and dialkyl carbonates such as tetrahydrofuran (THF), methyl acetate (MA), diglyme, trigylme, tetragylme, dimethyl carbonate (DMC), 1,2-dimethoxyethane (DME), 1,2-diethoxyethane (DEE), 1-ethoxy, 2-methoxyethane (EME), ethyl methyl carbonate, methyl propyl carbonate, ethyl propyl carbonate, diethyl carbonate, dipropyl carbonate, and mixtures thereof. High permittivity solvents include cyclic carbonates, cyclic esters and cyclic amides such as propylene carbonate (PC), ethylene carbonate (EC), butylene carbonate, acetonitrile, dimethyl sulfoxide, dimethyl formamide, dimethyl acetamide, γ-valerolactone, γ-butyrolactone (GBL), N-methylpyrrolidinone (NMP), and mixtures thereof. In the present invention, the preferred anode is lithium metal and the preferred electrolyte is 0.8M to 1.5M $LiAsF_6$ or $LiPF_6$ dissolved in a 50:50 mixture, by volume, of propylene carbonate and 1,2-dimethoxyethane.

Cells of the present invention having the first cathode material of a relatively lower energy density but a relatively higher power capability than that of the second cathode material are characterized by several voltage plateaus in their discharge profile. In the exemplary cell having SVO as the first cathode active material and $CF_x$ as the second cathode active material, the voltage profile initially follows the characteristic first voltage plateau of the SVO material at about 3.2 volts. The cell voltage then drops to another plateau at about 2.8 volts, which is primarily contributed by discharge of the $CF_x$ material. Then, the voltage profile follows the characteristic second plateau of the SVO material at about 2.6 volts. From about 2.5 volts to EOL (~2.0 volts) both the SVO and $CF_x$ materials contribute to cell discharge. Based on this, the capacity contribution from each voltage plateau region during cell discharge is highly dependent on the initial capacity ratio between the SVO and $CF_x$ materials ($SVO:CF_x$ ratio) in the cathode construction.

Therefore, by controlling the ratio of SVO to $CF_x$ in the cathode, it is possible to control the capacity contribution of the cell at various voltage plateau regions. For any device application, the ERI voltage (any voltage between about 2.65 volts to about 2.4 volts) and the EOL voltage (any voltage between about 2.5 volts to about 2.0 volts, or even lower for low rate cells) are defined. A particular cell is then designed by varying the SVO to $CF_x$ capacity ratio to meet any capacity requirements for ERI and EOL. The relationship is shown in equation 5:

$$A/B = [C \times SVO:CF_x \text{ ratio} + D]/(SVO:CF_x \text{ Ratio} + 1) \quad (5)$$

In equation 5, A is the defined capacity from ERI to EOL, B is the theoretical capacity of the cell, C is the efficiency of the SVO material in delivered capacity from ERI to EOL based on percent of the material's theoretical capacity, D is the efficiency of $CF_x$ material in delivered capacity from ERI to EOL based on percent of the material's theoretical capacity.

For example, a typical Li/SVO/$CF_x$ cell may be built having its ERI defined as a background discharge voltage of 2.6 volts and EOL defined as a background discharge voltage of 2.4V. Under these conditions, the estimated value for constants C and D are 32.1% and 13.8%, respectively. The C constant for SVO is estimated based on the 18 month accelerated discharge data (ADD) regime at 37° C. of a Li/SVO cell. The D constant for $CF_x$ is estimated based on the 18 month ADD at 37° C. (D=10.1%) and at 50° C. (D=17.6%) for a Li/$CF_x$ cell. An 18-month ADD regime consists of a pulse train comprising four 22 mA/cm$^2$ to 50 mA/cm$^2$, 10 second pulses with 15 seconds rest between each pulse. The pulse density is predicated on the cell capacity. One such pulse train is superimposed on the background load about every 45 days. The 18-month ADD is designed to deplete the cells of 100% of their theoretical capacity in 18 months.

If the total theoretical capacity of the cell (B) is known, the deliverable capacity from 2.6 volts (ERI) to 2.4 volts (EOL) is directly correlated with the $SVO:CF_x$ ratio, as shown in FIG. 1. The surface profile in this FIG. 1 demonstrates application of equation 5 in determining deliverable capacity between any two-background voltage points. For example, assume a Li/SVO/$CF_x$ cell having a theoretical capacity (B) of 2.5 Ah, as indicated by arrow 10 on the graph, and a $SVO:CF_x$ ratio of 1.1 (arrow 12). As discussed above, the C and D constants are 0.321 and 0.138, respectively. Curves 10 and 12 intersect at point 14 on the graph. From the above equation, the cell's discharge capacity (A) from ERI to EOL is determined to be about 0.58 volts. This corresponds with the graph by reading over to the ordinate from point 14 to find that the deliverable capacity from ERI to EOL is about 0.58 volts, as indicated by arrow 16.

It should be pointed out that many factors, such as the type of cathode active materials, discharge rate, discharge temperature, self-discharge rate, and cell design affect the magnitude of the C and D constants. The C and D constants set forth above and FIG. 1 are for a specific type of a Li/SVO/$CF_x$ cell. Other cell chemistries and types will have different graphs.

Figure 3:
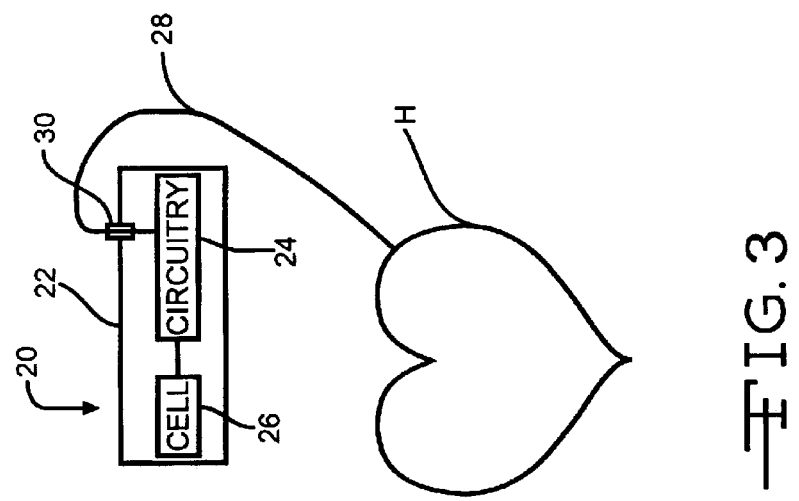
FIG. 3 is an enlarged schematic of the indicated area in FIG. 2 particularly showing the control circuitry 24 and the electrochemical cell 26 for the medical device 20 connected to the patient's heart H.
Figure 2:
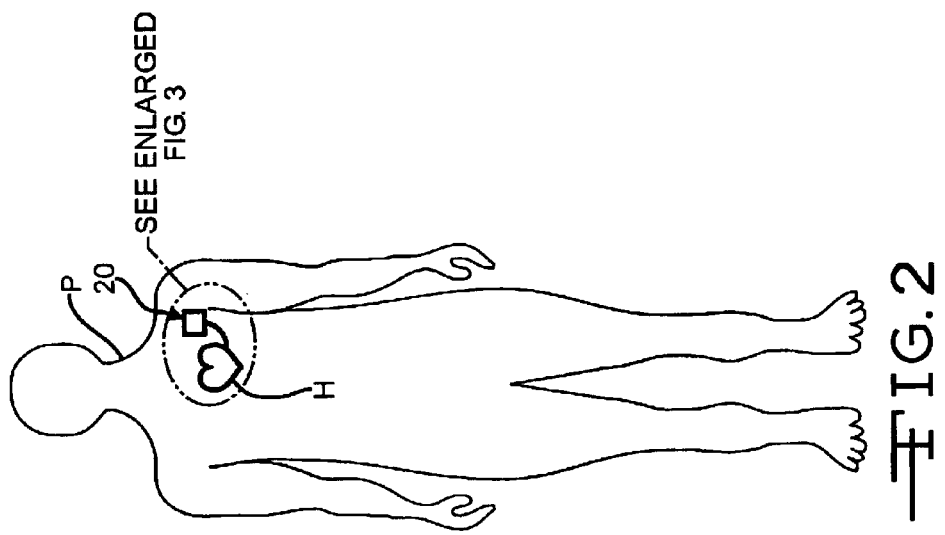
FIG. 2 is a schematic of a patient P provided with an implantable medical device 20.

FIGS. 2 and 3 show a patient P having a medical device 20, such as an implantable cardiac defibrillator, implanted inside the body. An enlarged schematic of the medical device 20 is shown in FIG. 3 comprising a housing 22 containing control circuitry 24 powered by an electrochemical cell 26 of the present invention. The control circuitry 24 is connected to at least one conductor 28 by a hermetic feedthrough 30, as is well known by those skilled in the art. The distal end of the conductor connects to the heart H for delivering a therapy thereto. Periodically, the patient will go to a medical facility, and the like, where the deliverable capacity determined by the control circuitry 24 is read to determine if the cell has discharged to the point that it is between the ERI and EOL voltages. If so, this indicates that it is time for the physician to schedule the patient for surgery to replace the medical device with a new one.

An important aspect of the present invention is that the SVO and $CF_x$ active materials reach end of life at the same time. This is the case in spite of the varied usage in actual implantable medical device application. Since both electrode materials reach end of service life at the same time, no energy capacity is wasted.

It is appreciated that various modifications to the inventive concepts described herein may be apparent to those of ordinary skill in the art without departing from the spirit and scope of the present invention as defined by the appended claims.

What is claimed is:

1. An implantable medical device, which comprises:
   a) a housing;
   b) a control circuitry contained inside the housing to control functioning of the medical device;
   c) an electrochemical cell contained inside the housing for powering the control circuitry, the cell comprising:
      i) an anode;
      ii) a cathode of a first cathode active material different than a second cathode active material, the first cathode active material being of a first energy density and a first rate capability and the second cathode active material being of a second energy density and a second rate capability, wherein the first cathode active material is contacted to one side of a current collector and facing the anode with the second cathode active material positioned on the opposite side of the current collector, and wherein the first energy density of the first cathode active material is less than the second energy density of the second cathode active material while the first rate capability of the first cathode active material is greater than the second rate capability of the second cathode active material; and
      iii) an electrolyte activating the anode and the cathode; and
   d) a conductor for connecting the medical device to a body intended to be assisted by the medical device;
   e) wherein the cell's discharge capacity (A) from an Elective Replacement Indicator voltage to an end-oflife (End of Life) voltage and a theoretical capacity (B) of the cell are determinable;

f) wherein the efficiencies of the first and second cathode active materials as (C) and (D), respectively, in terms of deliverable capacity from the A Elective Replacement Indicator voltage to the End of Life voltage are determinable; and g) wherein the cell's deliverable capacity from the Elective Replacement Indicator voltage to the End of Life voltage is determinable by the control circuitry using the equation: A/B=[C×a ratio of a first theoretical capacity of the first cathode active material:a second theoretical capacity of the second cathode active material+D]/(the ratio of the first theoretical capacity:the second theoretical capacity+1).

2. The medical device of claim 1 wherein the second cathode active material is selected from the group consisting of $CF_x$, $Ag_2O$, $Ag_2O_2$, $CuF$, $Ag_2CrO_4$, $MnO_2$, SVO, and mixtures thereof.

3. The medical device of claim 1 wherein the first cathode active material is selected from the group consisting of SVO, CSVO, $V_2O_5$, $MnO_2$, $LiCoO_2$, $LiNiO_2$, $LiMnO_2$, $CuO_2$, $TiS_2$, $Cu_2S$, FeS, $FeS_2$, copper oxide, copper vanadium oxide, and mixtures thereof.

4. The medical device of claim 1 wherein the cathode comprises first and second current collectors with the second cathode active material sandwiched between the current collectors, the cathode having the configuration: SVO/first current collector/$CF_x$/second current collector/SVO.

5. The medical device of claim 1 wherein the cathode comprises first and second current collectors with the second cathode active material sandwiched between the current collectors, the cathode having the configuration: SVO/first current collector/SVO/$CF_x$/SVO/second current collector/SVO.

6. The medical device of claim 1 wherein the anode is lithium and the cathode has the configuration: SVO/current collector/$CF_x$, with the SVO facing the lithium anode.

7. The medical device of claim 1 wherein the anode is lithium and the cathode has the configuration: SVO/current collector/SVO/$CF_x$, with the SVO facing the lithium anode.

8. An implantable medical device, which comprises:
a) a housing;
b) a control circuitry contained inside the housing to control functioning of the medical device;
c) an electrochemical cell for powering the medical device, the cell comprising:
  i) an anode;
  ii) a cathode of SVO as a first cathode active material and $CF_x$ as a second cathode active material, wherein the SVO is contacted to one side of a current collector and facing the anode with the $CF_x$ positioned on the opposite side of the current collector; and
  iii) an electrolyte activating the anode and the cathode; and
d) a conductor for connecting the medical device to a body intended to be assisted by the medical device;
e) wherein the cell's discharge capacity (A) from an Elective Replacement Indicator voltage to an end-of-life (End of Life) voltage and a theoretical capacity (B) of the cell are determinable;
f) wherein the efficiencies of the first and second cathode active materials as (C) and (D), respectively, in terms of delivered capacity from the Elective Replacement Indicator voltage to the End of Life voltage are determinable; and g) wherein the cell's deliverable capacity from the Elective Replacement Indicator voltage to the End of Life voltage is determinable by the control circuitry using the equation: A/B=[C×a ratio of a first theoretical capacity of the first cathode active material:a second theoretical capacity of the second cathode active material+D]/(the ratio of the first theoretical capacity:the second theoretical capacity+1).

9. The medical device of claim 8 wherein the Elective Replacement Indicator voltage is from about 2.65 volts to about 2.4 volts.

10. The medical device of claim 8 wherein the End of Life voltage is from about 2.5 volts to about 2.0 volts.

11. The medical device of claim 8 wherein the capacity ratio of SVO:$CF_x$ is from about 1:50 to about 10:1.

12. The medical device of claim 8 wherein the current collector is selected from the group consisting of stainless steel, titanium, tantalum, platinum, gold, aluminum, cobalt nickel alloys, highly alloyed ferritic stainless steel containing molybdenum and chromium, and nickel-, chromium-, and molybdenum-containing alloys.

13. The medical device of claim 8 including providing the current collector of titanium having a coating selected from the group consisting of graphite/carbon material, gold, iridium, palladium, platinum, rhodium, ruthenium, and mixtures thereof provided thereon.

14. The medical device of claim 8 wherein the cathode has the configuration: SVO/first current collector/$CF_x$/second current collector/SVO.

15. The medical device of claim 8 wherein the cathode has the configuration: SVO/first current collector/SVO/$CF_x$/SVO/second titanium current collector/SVO.

16. The medical device of claim 8 wherein the anode is lithium and the cathode has the configuration: SVO/current collector/$CF_x$, with the SVO facing the lithium anode.

17. The medical device of claim 8 wherein the anode is lithium and the cathode has the configuration: SVO/current collector/SVO/$CF_x$, with the SVO facing the lithium anode.

18. A method for providing an elective replacement indicator (Elective Replacement Indicator) for an implantable medical device, comprising the steps of:
a) providing the implantable medical device;
b) powering the medical device with an electrochemical cell, which comprises:
  i) an anode;
  ii) a cathode of a first cathode active material different than a second cathode active material, the first cathode active material being of a first energy density and a first rate capability and the second cathode active material being of a second energy density and a second rate capability, wherein the first cathode active material is contacted to one side of a current collector and facing the anode with the second cathode active material positioned on the opposite side of the current collector, and wherein the first energy density of the first cathode active material is less than the second energy density of the second cathode active material while the first rate capability of the first cathode active material is greater than the second rate capability of the second cathode active material; and
  iii) an electrolyte activating the anode and the cathode; and
c) determining the cell's discharge capacity (A) from an Elective Replacement Indicator voltage to an end-of-life (End of Life) voltage;
d) determining a theoretical capacity (B) of the cell;

e) determining the efficiencies of the first and second cathode active materials as (C) and (D), respectively, in terms of delivered capacity from the Elective Replacement Indicator voltage to the End of Life voltage;

f) determining the deliverable capacity of the cell from the Elective Replacement Indicator voltage to the End of Life voltage using the equation: A/B=[C×a ratio of a first theoretical capacity of the first cathode active material:a second theoretical capacity of the second cathode active material+D]/(the ratio of the first theoretical capacity:the second theoretical capacity+1);

g) implanting the medical device powered by the cell; and h) monitoring the cell's discharge capacity to determine when the Elective Replacement Indicator voltage is reached.

19. The method of claim 18 including selecting the second cathode active material from the group consisting of $CF_x$, $Ag_2O$, $Ag_2O_2$, CuF, $Ag_2CrO_4$, $MnO_2$, SVO, and mixtures thereof.

20. The method of claim 18 including selecting the first cathode active material from the group consisting of SVO, CSVO, $V_2O_5$, $MnO_2$, $LiCoO_2$, $LiNiO_2$, $LiMnO_2$, $CuO_2$, $TiS_2$, $Cu_2S$, FeS, $FeS_2$, copper oxide, copper vanadium oxide, and mixtures thereof.

21. The method of claim 18 wherein the cathode comprises first and second current collectors with the second cathode active material sandwiched between the current collectors, and providing the cathode having the configuration: SVO/first current collector/$CF_x$/second current collector/SVO.

22. The method of claim 18 wherein the cathode comprises first and second current collectors with the second cathode active material sandwiched between the current collectors, and providing the cathode having the configuration: SVO/first current collector/SVO/$CF_x$/SVO/second current collector/SVO.

23. The method of claim 18 wherein the anode is lithium and the cathode has the configuration: SVO/current collector/$CF_x$, with the SVO facing the lithium anode.

24. The method of claim 18 wherein the anode is lithium and the cathode has the configuration: SVO/current collector/SVO/$CF_x$, with the SVO facing the lithium anode.

25. A method for providing an elective replacement indicator Elective Replacement Indicator, for an implantable medical device, comprising the steps of:

a) providing the implantable medical device;

b) powering the medical device with an electrochemical cell, which comprises:

i) an anode;

ii) a cathode of SVO as a first cathode active material and $CF_x$ as a second cathode active material, wherein the SVO is contacted to one side of a current collector and facing the anode with the $CF_x$ positioned on the opposite side of the current collector; and iii) an electrolyte activating the anode and the cathode; and c) determining the cell's discharge capacity (A) from an Elective Replacement Indicator voltage to an end-of-life (EOL) voltage;

d) determining a theoretical capacity (B) of the cell;

e) determining the efficiencies of the SVO and $CF_x$ materials as (C) and (D), respectively, in terms of delivered capacity from the Elective Replacement Indicator voltage to the End of Life voltage;

f) determining the deliverable capacity of the cell from the Elective Replacement Indicator voltage to the End of Life voltage using the equation: A/B=[C×a ratio of a first theoretical capacity of the SVO:a second theoretical capacity of the $CF_x$+D]/(the ratio of the first theoretical capacity:the second theoretical capacity+1);

g) implanting the medical device powered by the cell; and h) monitoring the cell's discharge capacity to determine when the Elective Replacement Indicator voltage is reached.

26. The method of claim 25 including selecting the Elective Replacement Indicator voltage from about 2.65 volts to about 2.4 volts.

27. The method of claim 25 including selecting the End of Life voltage from about 2.5 volts to about 2.0 volts.

28. The method of claim 25 including selecting the capacity ratio of SVO:$CF_x$ from about 1:50 to about 10:1.

29. The method of claim 25 including selecting the current collector from the group consisting of stainless steel, titanium, tantalum, platinum, gold, aluminum, cobalt nickel alloys, highly alloyed ferritic stainless steel containing molybdenum and chromium, and nickel-, chromium-, and molybdenum-containing alloys.

30. The method of claim 25 including providing the current collector of titanium having a coating selected from the group consisting of graphite/carbon material, gold, iridium, palladium, platinum, rhodium, ruthenium, and mixtures thereof provided thereon.

31. The method of claim 25 wherein the cathode has the configuration: SVO/first current collector/$CF_x$/second current collector/SVO.

32. The method of claim 25 wherein the cathode has the configuration: SVO/first current collector/SVO/$CF_x$/SVO/second current collector/SVO.

33. The method of claim 25 wherein the anode is lithium and the cathode has the configuration: SVO/current collector/$CF_x$, with the SVO facing the lithium anode.

34. The method of claim 25 wherein the anode is lithium and the cathode has the configuration: SVO/ current collector/SVO/$CF_x$, with the SVO facing the lithium anode.

* * * * *

UNITED STATES PATENT AND TRADEMARK OFFICE
CERTIFICATE OF CORRECTION

PATENT NO. : 6,936,379 B2
DATED : August 30, 2005
INVENTOR(S) : Gan et al.

It is certified that error appears in the above-identified patent and that said Letters Patent is hereby corrected as shown below:

Column 8, line 67 - Column 9, line 1,
"end-of-life (End of Life)" should read -- End of Life --;

Column 9,
Line 5, "A Elective" should read -- Elective --;
Lines 60-61, "end-of-life (End of Life)" should read -- End of Life --;

Column 10,
Lines 39-40, "elective replacement indicator (Elective Replacement Indicator)" should read -- Elective Replacement Indicator --;
Lines 65-66, "end-of life (End of Life)" should read -- End of Life --;

Column 11,
Lines 42-43, please delete "elective replacement indicator", first occurrence; and Column 12,
Lines 5-6, "end-of-life (EOL)" should read -- End of Life --.

Signed and Sealed this

First Day of November, 2005

JON W. DUDAS
*Director of the United States Patent and Trademark Office*